United States Patent [19]

Stephens

[11] Patent Number: 5,560,096
[45] Date of Patent: Oct. 1, 1996

[54] METHOD OF MANUFACTURING FEMORAL KNEE IMPLANT

[75] Inventor: Ron Y. Stephens, Memphis, Tenn.

[73] Assignee: Smith & Nephew Richards Inc., Memphis, Tenn.

[21] Appl. No.: 376,930

[22] Filed: Jan. 23, 1995

[51] Int. Cl.$^6$ .................................................. B23P 13/04
[52] U.S. Cl. .................... 29/558; 29/527.6; 451/21; 623/20
[58] Field of Search ................................ 29/527.2, 527.3, 29/527.6, 558, 160.6, 81.11, 56.5, 33 C, 81.01; 451/21, 158; 623/20, 18

[56] References Cited

U.S. PATENT DOCUMENTS

| | | | |
|---|---|---|---|
| 3,654,692 | 4/1972 | Goetz | 29/558 |
| 4,611,373 | 9/1986 | Hazebrook | 29/558 X |
| 4,753,044 | 6/1988 | Bula | 451/65 |
| 5,092,022 | 3/1992 | Duret | 29/160.6 |
| 5,100,409 | 3/1992 | Coates et al. | 623/20 X |

*Primary Examiner*—Peter Vo
*Assistant Examiner*—Khan V. Nguyen
*Attorney, Agent, or Firm*—Pravel, Hewitt, Kimball & Krieger

[57] ABSTRACT

A method of manufacturing a distal femoral knee prosthesis includes the initial step of forming a rough prosthesis workpiece member that has the approximate size and shape of a final polished distal femoral prosthesis. The rough prosthesis workpiece member can be a casting, forging or a rough machined part. The prosthesis member is then attached to a fixator and movably supported adjacent a rotary grinder. Relative motion between the rotary grinder and the prosthesis is controlled with a computer. An articular surface of the prosthesis is shaped by engaging the prosthesis with the rotary grinder. The workpiece is primarily polished to remove "scallops" that form on the outer surface during a shaping with the rotary grinder. The prosthesis workpiece member is then secondarily polished until the articular surface provides a highly polished mirror finish.

18 Claims, 6 Drawing Sheets

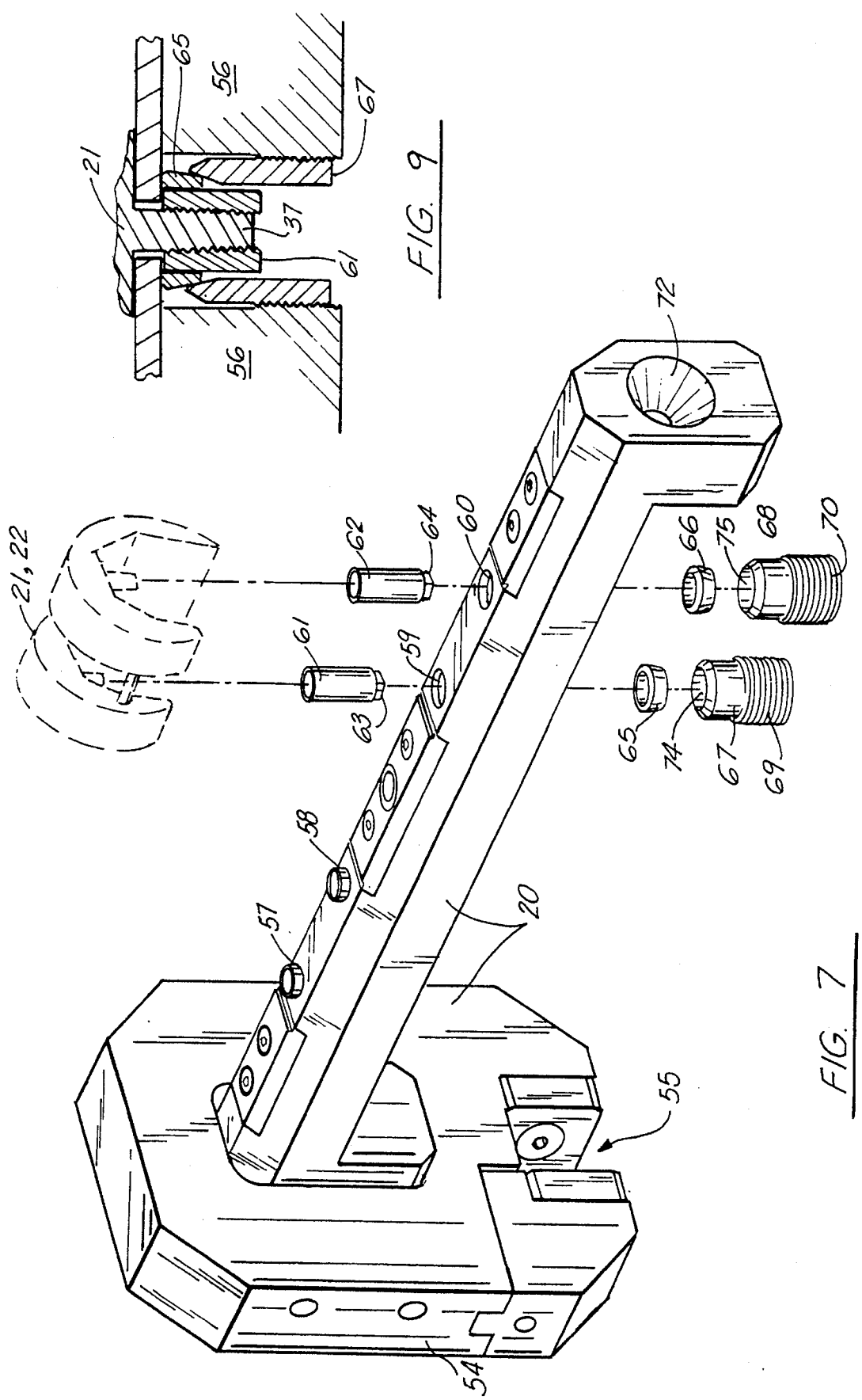

METHOD OF MANUFACTURING FEMORAL KNEE IMPLANT

BACKGROUND OF THE INVENTION:

1. Field of the Invention

The present invention relates to surgical orthopedic implants and methods of manufacturing same. Even more particularly, the present invention relates to an improved orthopedic joint implant component (e.g. femoral component) having a non articulating surface that fastens the implant to the patient's bone tissue adjacent the joint to be replaced and an articulating surface that engages a corresponding implant member (e.g. tibial component) and wherein the articulating surface is dressed using a programmable CNC multi-axis grinder that cuts multiple parallel grooves in the articulating surface of a blank (e.g. cast, forged, machined) as the blank is oscillated about a first axis on a fixture and translated during such oscillation to define the shape of the articular surface being cut, subsequent method steps including a coarse polishing to remove "peaks" formed by the grinder, followed by a fine polishing of the articular surface.

2. General Background

Prosthetic joint devices are well known in the art. One of the most common types of joint prosthetic devices is a knee prosthesis that includes a femoral component and a tibial component. The femoral component typically has a "J" shape and includes a distal articulating surface with anterior, distal and posterior condylar portions. The non-articulating surface of the prosthesis includes a number of flat intersecting surfaces that mate with similarly shaped surfaces surgically formed on the patient's distal femur.

One of the problems that has plagued the manufacture of femoral knee implants is that of proper sizing and shaping. The distal femoral articulating surface is a complex structure. In the past, sizing and shaping this structure has been a highly labor intensive process that requires a number of manual polishing steps. However, these polishing steps are typically performed by workers that do not exactly duplicate the same shape each time. Variations can occur even at the same factory between two different workers.

SUMMARY OF THE INVENTION

The present invention solves this prior art problem by providing a highly effective and controllable method of manufacturing a distal femoral knee prosthesis.

The method of the present invention begins with the formation of a rough prosthesis workpiece member that has the approximate size and shape of a final polished distal femoral prosthesis.

The workpiece can be a cast metallic part for example. The prosthesis member is attached to a fixator. The fixator is movably supported adjacent a rotary grinder wheel. A computer is used to control relative motion between the rotary grinder and the prosthesis workpiece member.

A curved "J" shaped articular surface of the prosthesis member is formed by engaging the prosthesis with the rotating rotary grinder wheel.

In the preferred method, the grinding wheel sculpts the articular surface by forming a plurality of generally parallel grooves adjacent one another. This also forms "peaks" at the intersections of two adjacent grooves sculpted by the grinding wheel. The articulating surface of the workpiece is preliminarily polished to remove peaks that occur between adjacent grooves cut by the rotary grinder wheel. Thereafter, the articular surface is secondarily polished until it has a highly polished mirror finish.

In the preferred method, the rotary grinder and the fixator each have central longitudinal axes. These axes are maintained generally parallel during a shaping of the articular surface of the prosthesis member with the grinder wheel.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 7 is a fragmentary exploded perspective view of the preferred embodiment of the apparatus of the present invention;

FIG. 9 is a fragmentary sectional view of the preferred embodiment of the apparatus of the present invention illustrating the attachment between the prosthesis component and grinding fixture;

DETAILED DESCRIPTION OF THE PREFERRED EMBODIMENT

Figure 1:
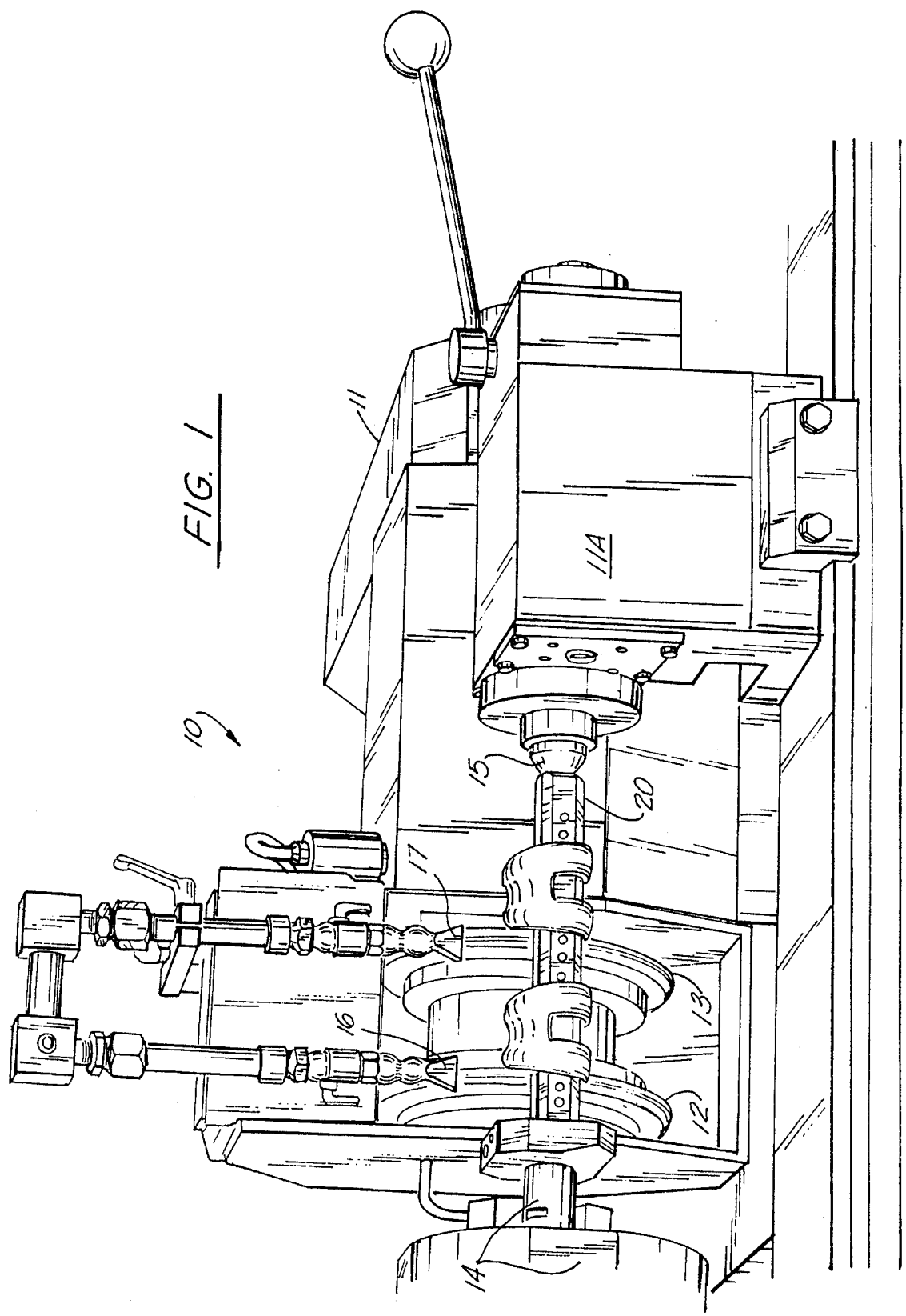
FIG. 1 is a perspective view of the preferred embodiment of the apparatus of the present invention.
Figure 2:
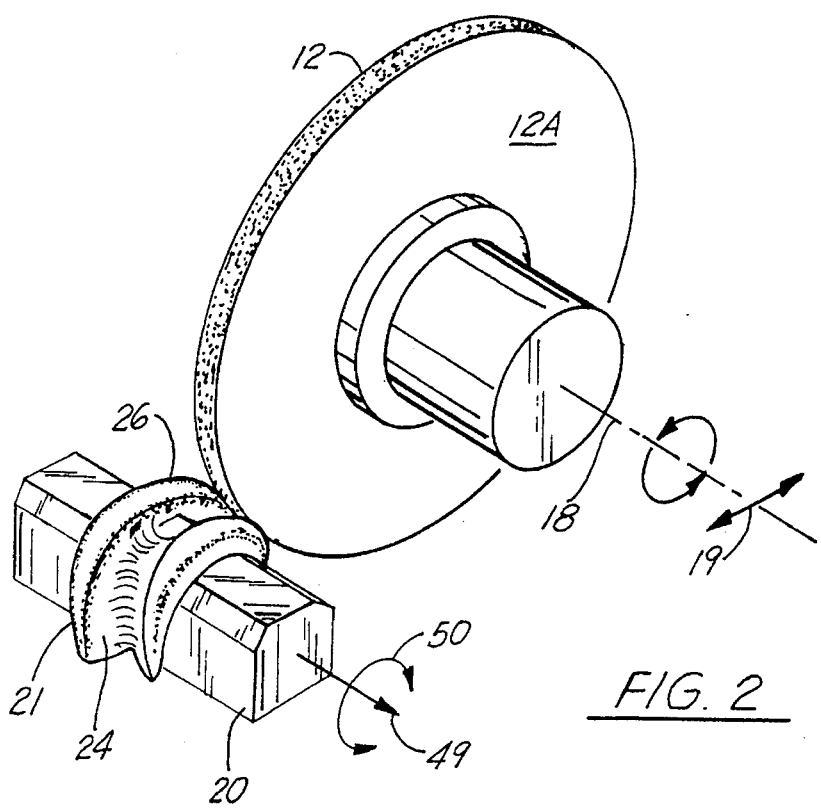
FIG. 2 is a fragmentary perspective view of the preferred embodiment of the apparatus of the present invention.
Figure 3:
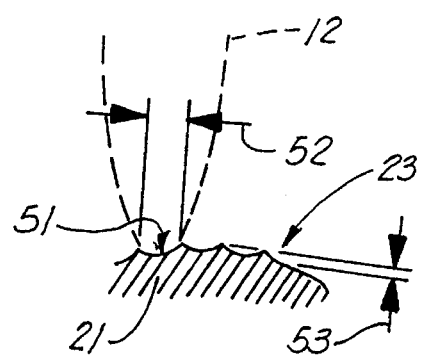
FIG. 3 is a fragmentary schematic view illustrating the grinding step of the method of the present invention.

FIGS. 1–3 show the preferred embodiment of the apparatus of the present invention designated generally by the numeral 10. Prosthesis grinding apparatus 10 includes a grinding fixture 20 supported between work head 14 and a tailstock 11A in a conventional programmable CNC multi-axis grinder 11 that includes for example a pair of spaced apart rotary grinding wheels 12, 13 and spaced apart holding portions 14, 15. The holding portions 14, 15 interface with end portions of the grinding fixture 20 after prosthesis component workpieces 21, 22 are attached thereto. Workpieces 20,21 include femoral component workpiece 21 and femoral component workpiece 22.

Programmable grinder 11 can include fluid dispensers for dispensing a desired cooling fluid to the grinding apparatus as is known in the art. Such fluid dispensers 16, 17 are typically supplied with commercial available programmable grinders 11, a fluid dispenser 16, 17 being positioned respectively above each grinding wheel 12, 13.

In FIG. 2, the axis of rotation 18 of grinding wheel 12 is illustrated. The grinding wheel 12 rotates about axis 18. Wheel 12 also moves in an anterior/posterior direction relative to the workpiece 21 along an anterior/posterior direction created by relative movement between path 19 and 50 in FIG. 2.

In combination with the rotary movement of grinder 12 and its for and aft movement along path 19, there is also provided relative movement between grinding wheel 12 and prosthesis component 21 by moving grinding fixture 20. In FIG. 2, arrows 49 indicate schematically lateral/medial movement of grinding fixture 20 relative to wheel 12. The plane of wheel 12 is designated as 12A. Curved arrow 50 schematically illustrates rotation in an anterior posterior direction of the component 21 relative to wheel 12.

The programmable grinder 11 can thus be programmed to rotate the wheel 12 at a desired speed, move the wheel for and aft along the path 19 a desired degree during cutting of the prosthesis 21, and rotate the grinding fixture 20 about its central longitudinal axis. This combination presents various anterior, distal, and posterior articulating surfaces of the femoral component workpiece 21 to the grinding wheel 12. In this fashion, grooves or scallop is formed in the articulating 23 surface of the selected component workpiece 21 or 22 as shown in FIG. 3. The grooves or scallops are designated as 51 in FIG. 3. Grooves 51 are spaced apart by measure that is designated by the arrows 52 in FIG. 3 as groove spacing. Further, each of the grooves have a thickness that is designated by the arrows 53 in FIG. 3.

Figure 4:
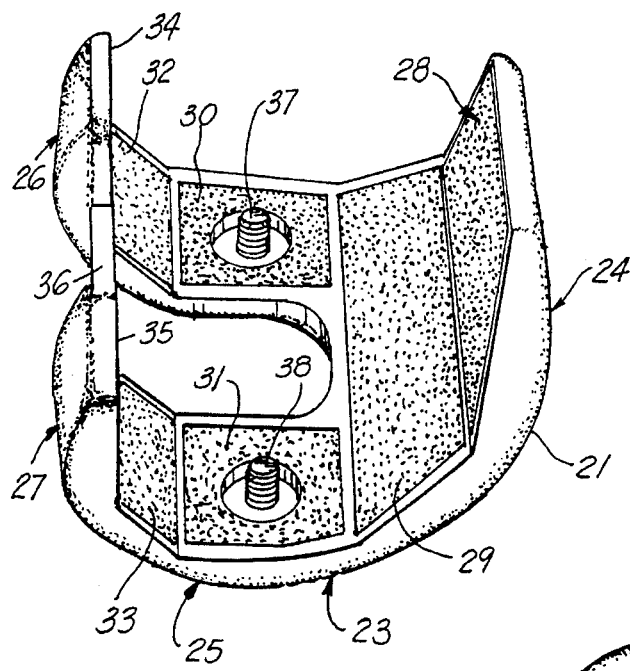
FIG. 4 is a perspective view of a prosthesis workpiece to be finished using the method of the present invention.
Figure 5:
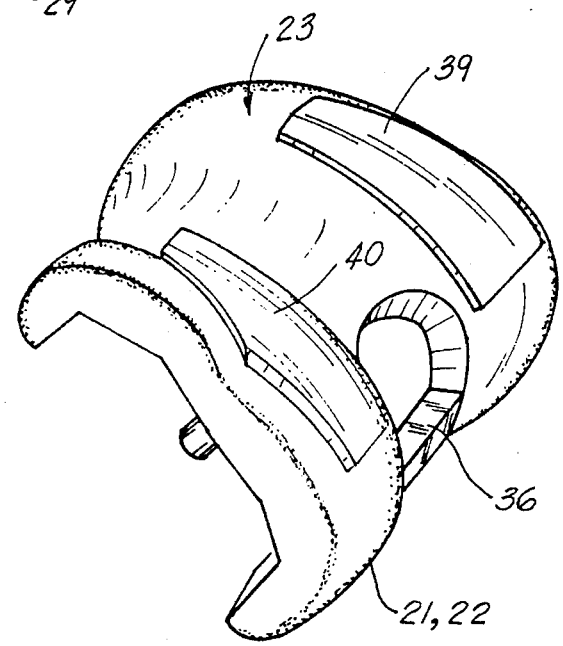
FIG. 5 is another perspective view of a prosthesis workpiece to be finished using the method of the present invention.
Figure 6:
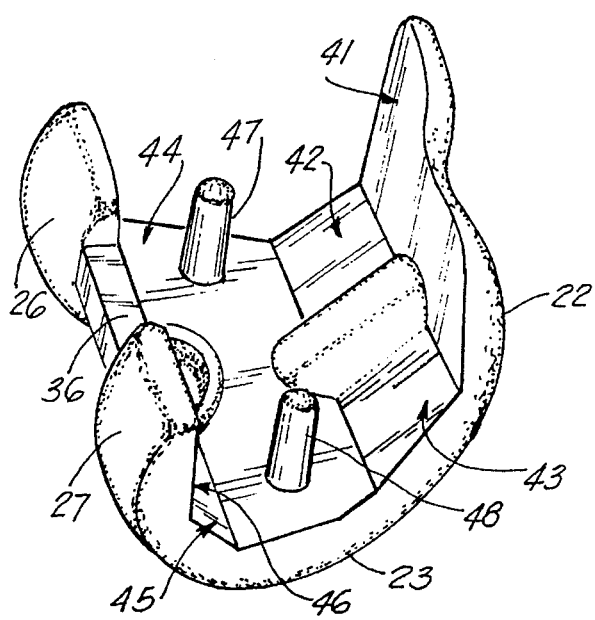
FIG. 6 is a perspective view of another prosthesis to be finished using the method of the present invention.

In FIGS. 4–6, two femoral component workpiece 21, 22 are shown for purposes of illustration. In FIG. 4, femoral component workpiece 21 is provided with threaded attachments 37, 38 and with a bone ingrowth surface that is comprised of a plurality of non-articulating surfaces 28–35. In FIGS. 5 and 6, femoral component workpiece 22 is provided with unthreaded, smooth attachment posts 47, 48.

In FIG. 4, the femoral component workpiece 21 includes an outer, articulating surface 23 that is to be dressed using the method and apparatus of the present invention. The articulating surface 23 includes an anterior end surface 24, a distal end surface 25, and a pair of spaced apart posterior condylar surfaces 26, 27. The non-articulating surfaces 28–35 include anterior non-articulating surface 28, chamfer surfaces 29 and 32–33, distal non-articulating surfaces 30, 31 and posterior condylar non-articulating surfaces 34, 35. Transverse bar 36 can form a connection between condylar portions of the prosthesis workpiece 24 that are covered with exterior condylar surfaces 26, 27 and with the surfaces 34, 35.

In FIG. 4, the attachment posts 37, 38 are threaded. These threaded posts 37, 38 must be protected from damage when component 21 is subjected to programmable grinder 11 according to the method of the present invention as will be described more fully hereinafter.

In FIG. 6, component 22 includes smooth surfaces 41–46 and smooth posts 47, 48. The surface 41 is an anterior surface. The surfaces 42–43 and 45 are chamfer surfaces. Surface 44 is a distal non-articulating surface. Surface 46 is a posterior non-articulating surface. In each of the workpiece of FIGS. 4 and 6, the rear non-articulating surfaces 28–35 and 41–46 are surfaces that register with similarly shaped cut surfaces on the patient's distal femur as prepared by a surgeon.

In FIG. 5, workpieces 21, 22 is shown and more specifically the articulating surface 23 thereof. The present invention provides an improved method for shaping such workpieces 21, 22 having articulating surfaces 23. These workpieces 21, 22 which begin as castings, rough machinings, forgings or the like. For example, if workpieces 21, 22 begin as castings, they can have projecting portions 39, 40 that are formed during casting and which must be removed as part of the method of the present invention.

FIG. 7 illustrates a more detailed view of grinding fixture 20. Grinding fixture 20 has an enlarged end portion 54 held by grinder 11 holder 14. End portion 54 provided a recess 55 that can be engaged by a torquing member for imparting rotation to the grinding fixture 20 as generated by the programmable grinder 11. The grinding fixture 20 includes an elongated bar 56 having a plurality of cylindrically shaped openings 57–60, each of the openings 57–60 having a central longitudinal axis that is perpendicular to the axis of rotation of the grinding fixture 20. In FIG. 2, the axis of rotation of grinding fixture 20 is defined by arrow 49.

Because each of the cylindrical openings 57–60 has an axis that is perpendicular to the axis of rotation of fixture 20, this similarly places each of the non-articulating surfaces 28–35 of prosthesis workpiece 21 and 41–46 of prosthesis 22 at right angles to the anterior posterior travel path 19 of grinding wheel 12 and also at right angles to the plane of grinding wheel 12 designated as 12A in FIG. 2.

Figure 8:
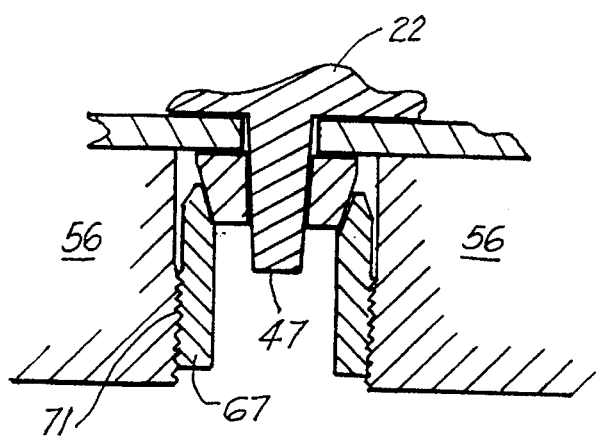
FIG. 8 is a fragmentary sectional view of the preferred embodiment of the apparatus of the present invention illustrating the attachment between the prosthesis component and grinding fixture.

FIGS. 8–9 show the connection formed between a post 37, 47 of a component workpiece 21 or 22 and the elongated transverse bar 56 of fixture 20. In FIG. 9, the sectional view illustrates the connection formed between component 22 and bar 56 of fixture 20. When a component workpiece 21 is to be connected to fixture 20 and the component workpiece 21 has threaded attachment posts such as 37, a thread protector 61, 62 is threadably attached to the threaded attachment post 37, 38. Thread protector 61, 62 provides an internal threaded bore with internal threads that match the external threads of the posts 37, 38.

Each of the thread protectors 61, 62 can have a hexagonal drive portion 63, 64 to aid in a solid attachment of the particular thread protector 61, 62 to a selected of the threaded posts 37, 38.

In FIG. 9, a thread protector 61 has been applied to a threaded attachment post 37. In order to complete an attachment of the workpiece 21 to the grinding fixture 20, the user places annular sleeve 65 or 66 over the thread protector 61, 62 as shown in FIGS. 7 and 9.

Threaded sleeves 67, 68 then extends over the thread protector 61 and ferrule 65 as shown in FIG. 9. The threaded sleeve 67, 68 have external threads 69, 70 that engage corresponding internal threads 71 that line a portion of the selected opening 59, 60 as shown in FIG. 9. Each of the threaded sleeves 67, 68 each provide beveled annular surfaces 74, 75 respectively that engage the outer surface of ferrules 65, 66 for forming a wedge lock connection therewith. As the user tightens the selected threaded sleeve 67, 68, the selected components 21, 22 is rigidly connected to grinding fixture 20.

In FIG. 8, a connection is shown between prosthesis component workpiece 22 having a smooth attachment post 47 and the grinding fixture 20. In FIG. 8, annular sleeve 65 connects directly to the unthreaded attachment post 47. Threaded sleeve 67 then engages the threads 71 of bar 56 to form a wedge lock connection between the beveled annular surface 74 of sleeve 67 and the outer surface of the annular sleeve 65.

Figure 11:
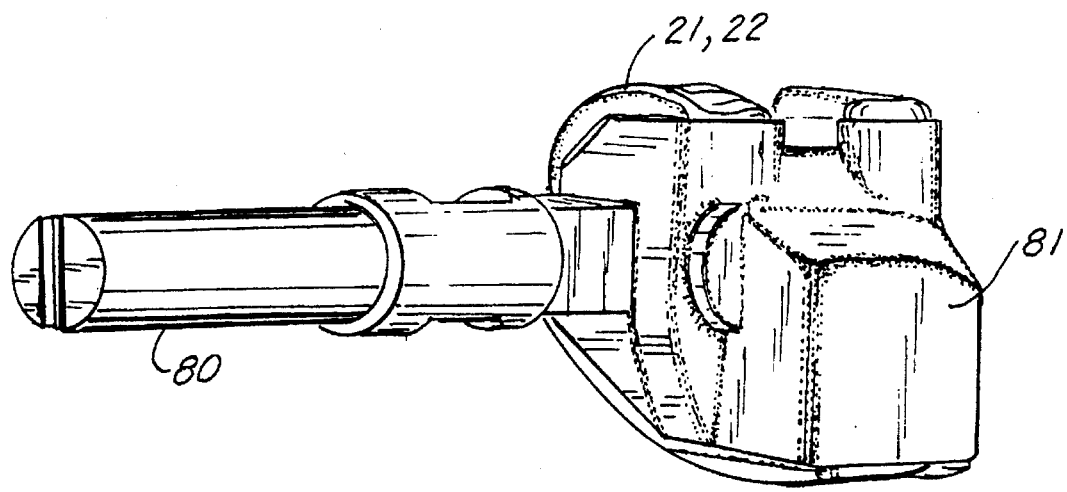
FIG. 11 is a fragmentary perspective view of the preferred embodiment of the apparatus of the present invention illustrating the coarse polishing fixture portion thereof.
Figure 10:
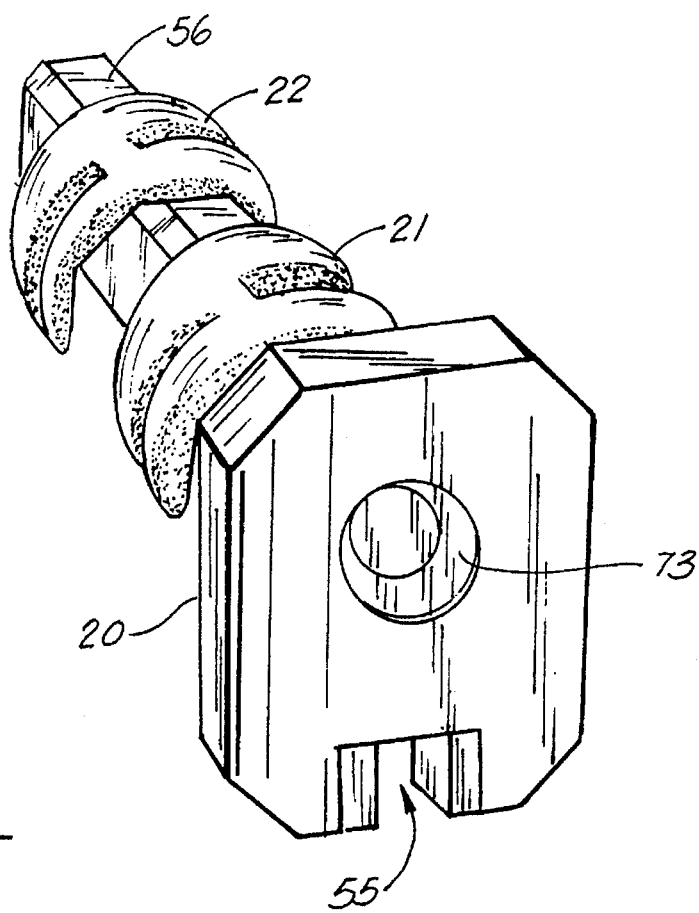
FIG. 10 is a fragmentary perspective end view of the preferred embodiment of the apparatus of the present invention illustrating the grinding fixture.

After the plurality of grooves or scallops 51 are formed in the external surface 23 (i.e. the articulating surface 23 of the selected femoral component workpiece 21, 22 the component workpiece 21, 22 is first subjected to a coarse polishing. During the coarse polishing each component workpiece 21, 22 is affixed to a polishing fixture 80 as shown in FIG. 11. The connection between the selected component workpiece 21, 22 and the elongated bar like fixture 80 can be the same type of connection as with the fixture 20 as shown in FIGS. 7, 8, and 9.

In order to protect all but the articulating surface from the coarse polishing, urethane protector block 81 is added to the component workpiece 21 or 22 as shown in FIG. 11. Protector block 81 can be of urethane plastic for example and extend both in a lateral medial direction and in an anterior posterior direction so that all of the non-articulating surfaces 28-25 or 41-46 are covered and protected from contact with polishing media 90 during the coarse polishing.

Figure 12:
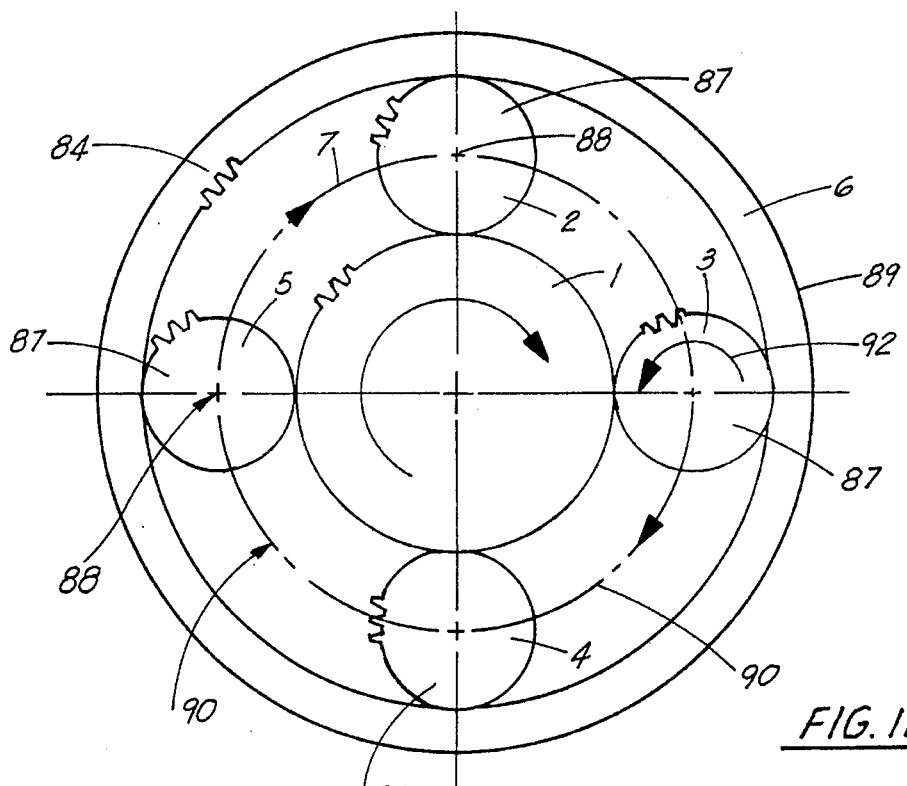
FIGS. 12–13 are schematic views illustrating the coarse polishing step of the method of the present invention.
Figure 13:
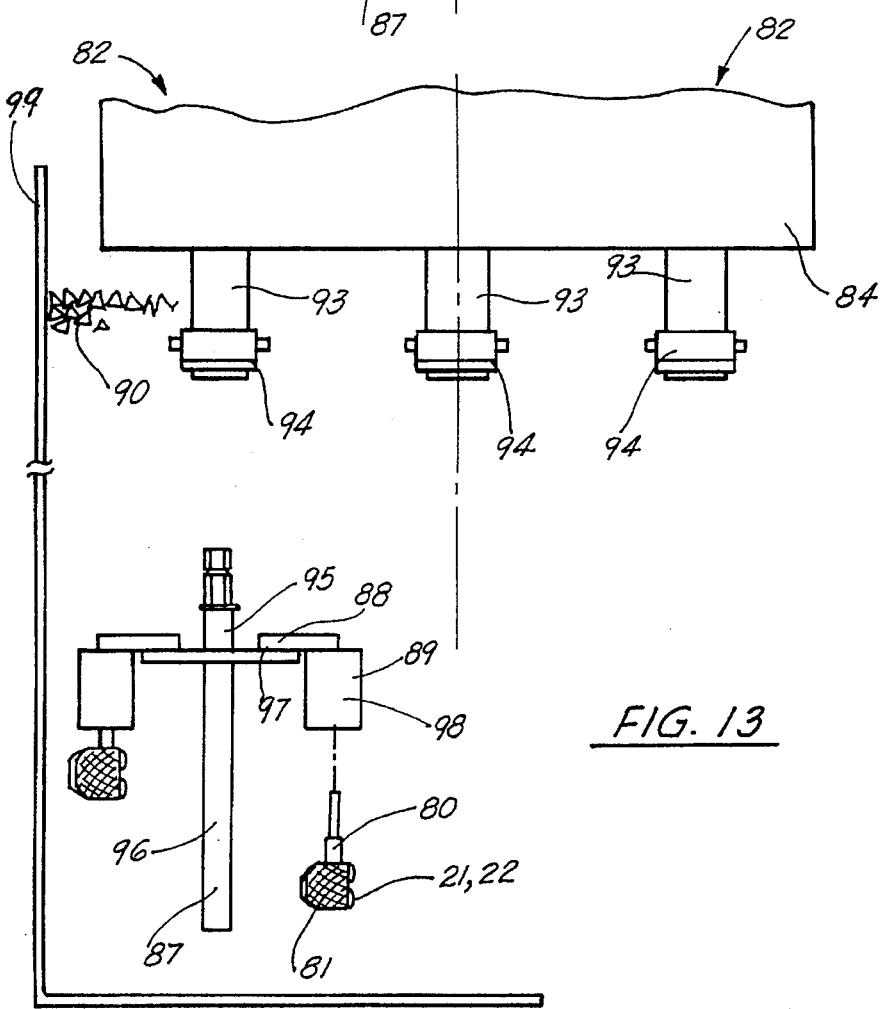

In FIGS. 12-13, the coarse polishing method step is schematically shown. In FIGS. 12-13 there can be seen a motor drive 83 that powers and rotates a sun gear 85 within gear case 84. The gear case 84 includes motor driven sun gear 85 having axis of rotation 86. Sun gear 85 is powered to rotate and drive a plurality of four planetary gears 87, each having an axis of rotation 88. An outer housing gear 89 surrounds and engages the planetary gears 87 and sun gear 85.

In FIG. 12, a circular path 90 indicates the travel path followed by of each of the planetary gears 88. Curved arrow 91 indicates the direction of rotation of the sun gear 85. Curved arrow 92 indicates the direction of rotation of the planetary gears 87.

In FIG. 13, the planetary gear case 84 is shown having a plurality of extensions shafts 93 extending downwardly therefrom, each attached respectively to a planetary gear 87 within planetary gear case 84. Each of the extension shafts 93 carries a chuck 94 for holding a holding fixture 95.

The holding fixture 95 includes a vertical shaft 96, a plurality of circumferentially spaced, radially extending arms 97, and a plurality of holders 98 that can form an attachment with the polishing fixture 80.

The plurality of holding fixtures 95 are supported within a tank 99 that contains media 90, a commercially available polishing media. Rotation of the fixtures 95 within tank 99 and the contained media 90 removes the scallops formed on the articulating surface of each workpiece 21, 22.

After coarse polishing, the component workpiece 21, 22 can be finely polished using a commercially available computer controlled polishing machine such as shown and described in U.S. Pat. 4,753,044 which is incorporated herein by reference.

The following table lists the parts numbers and parts descriptions as used herein and in the drawings attached hereto:

PARTS LIST

| Part Number | Description |
| --- | --- |
| 10 | prosthesis grinder apparatus |
| 11 | grinder |
| 11A | grinder tailstocks |

-continued

PARTS LIST

| Part Number | Description |
| --- | --- |
| 12 | grinding wheel |
| 12A | plane of rotation |
| 13 | grinding wheel |
| 14 | grinder workhead |
| 15 | tailstock center |
| 16 | fluid dispenser |
| 17 | fluid dispenser |
| 18 | axis of rotation of grinding wheel |
| 19 | path |
| 20 | grinding fixture |
| 21 | femoral component workpiece |
| 22 | femoral component workpiece |
| 23 | articulating surface |
| 24 | anterior end |
| 25 | distal end |
| 26 | posterior condylar surface |
| 27 | posterior condylar surface |
| 28 | non-articulating surface |
| 29 | non-articulating surface |
| 30 | non-articulating surface |
| 31 | non-articulating surface |
| 32 | non-articulating surface |
| 33 | non-articulating surface |
| 34 | non-articulating surface |
| 35 | non-articulating surface |
| 36 | transverse bar |
| 37 | attachment post |
| 38 | attachment post |
| 39 | casting gate |
| 40 | casting gate |
| 41 | anterior surface |
| 42 | chamfer surface |
| 43 | chamfer surface |
| 44 | distal surface |
| 45 | chamfer surface |
| 46 | posterior surface |
| 47 | attachment post |
| 48 | attachment post |
| 49 | arrow |
| 50 | curved arrow |
| 51 | scallop |
| 52 | scallop spacing |
| 53 | scallop height |
| 54 | enlarged end |
| 55 | recess |
| 56 | elongated bar |
| 57 | opening |
| 58 | opening |
| 59 | opening |
| 60 | opening |
| 61 | thread protector |
| 62 | thread protector |
| 63 | hex drive |
| 64 | hex drive |
| 65 | ferrule |
| 66 | ferrule |
| 67 | threaded sleeve |
| 68 | threaded sleeve |
| 69 | external threads |
| 70 | external threads |
| 71 | internal threads |
| 72 | conical socket |
| 73 | conical socket |
| 74 | annular surface |
| 75 | annular surface |
| 80 | polishing fixture |
| 81 | protector block |
| 82 | coarse polisher |
| 83 | motor drive |
| 84 | planetary gear case |
| 85 | sun gear |
| 86 | axis of rotation |
| 87 | planetary gear |
| 88 | axis of rotation |
| 89 | housing gear |

-continued

PARTS LIST

| Part Number | Description |
|---|---|
| 90 | circular path |
| 91 | curved arrow |
| 92 | curved arrow |
| 93 | extension shaft |
| 94 | chuck body |
| 95 | holding fixture |
| 96 | shaft |
| 97 | arm |
| 98 | holder |
| 99 | tank |
| 100 | media |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of manufacturing a distal femoral knee prosthesis comprising the steps of:

a) forming a rough prosthesis workpiece member that has the approximate size and shape of a final, polished distal femoral prosthesis the workpiece member including a generally "J" shaped articular surface portion to be finished;

b) attaching the prosthesis member to a fixator;

c) movably supporting the fixator adjacent a rotary grinder wheel;

d) controlling relative motion between the rotary grinder and the prosthesis member workpiece with a computer;

e) shaping a curved articular surface of the prosthesis member by engaging the prosthesis member with the rotary grinder wheel that forms a plurality of grooved portions;

f) preliminary polishing the articular surface to remove the grooved portions; and g) secondarily polishing the articular surface until it has a highly polished mirror finish.

2. The method of claim 1 further comprising the forming of a pair of spaced apart, "J" shaped condylar portions in step "a" on the prosthesis member.

3. The method of claim 1 further comprising the step of moving the fixator about a central longitudinal axis of the fixator.

4. The method of claim 3 wherein the rotary grinder wheel and the fixator have central longitudinal axes and the axes are maintained generally parallel during a shaping of the articular surface of the prosthesis member.

5. The method of claim 1 wherein in step "f" the preliminary polishing includes polishing the prosthesis with a polishing media.

6. A method of manufacturing a distal femoral knee prosthesis comprising the steps of:

a) forming a rough prosthesis workpiece member that has the approximate size and shape of a final, polished distal femoral prosthesis;

b) attaching the prosthesis member to a fixator;

c) movably supporting the fixator adjacent a rotary grinder wheel;

d) controlling relative motion between the rotary grinder and the prosthesis member workpiece with a computer;

e) shaping a curved articular surface of the prosthesis member by engaging the prosthesis member with the rotary grinder wheel;

f) preliminary polishing the articular surface;

g) secondarily polishing the articular surface until it has a highly polished mirror finish; and h) wherein in step "e" the grinding wheel sculpts the articular surface by forming a plurality of grooves placed adjacent one another.

7. A method of manufacturing a distal femoral knee prosthesis comprising the steps of:

a) forming a rough prosthesis workpiece member that has the approximate size and shape of a final, polished distal femoral prosthesis;

b) attaching the prosthesis member to a fixator;

c) movably supporting the fixator adjacent a rotary grinder wheel;

d) controlling relative motion between the rotary grinder and the prosthesis member workpiece with a computer;

e) shaping a curved articular surface of the prosthesis member by engaging the prosthesis member with the rotary grinder wheel that forms a plurality of grooved portions;

f) preliminary polishing the articular surface to remove the grooved potions;

g) secondarily polishing the articular surface until it has a highly polished mirror finish; and h) wherein in step "a" the forming step includes forming a generally "J" shaped outer surface on the prosthesis member.

8. A method of manufacturing a distal femoral knee prosthesis comprising the steps of:

a) forming a rough prosthesis workpiece member that has the approximate size and shape of a final, polished distal femoral prosthesis;

b) attaching the prosthesis member to a fixator;

c) movably supporting the fixator adjacent a rotary grinder wheel;

d) controlling relative motion between the rotary grinder and the prosthesis member workpiece with a computer;

e) shaping a curved articular surface of the prosthesis member by engaging the prosthesis member with the rotary grinder wheel that forms a plurality of grooved portions;

f) preliminary polishing the articular surface to remove the grooved portions;

g) secondarily polishing the articular surface until it has a highly polished mirror finish h) wherein in step "a" the forming step includes forming a generally "J" shaped outer surface on the prosthesis member; and i) forming of a plurality of flat inner surfaces opposite the outer surface.

9. The method of claim 5 further wherein there are three inner flat surfaces formed on the workpiece opposite the outer surface.

10. A method of manufacturing a joint prosthesis comprising the steps of:

a) forming a rough joint prosthesis workpiece member that has the approximate size and shape of a desired final, polished joint prosthesis;

b) attaching the joint prosthesis member to a fixator;

c) supporting the fixator adjacent a rotary grinder;

d) controlling relative motion between the rotary grinder and the prosthesis member with a computer;

e) shaping an articular surface of the prosthesis member by engaging the prosthesis member with the rotary grinder;

f) preliminarily polishing the articular surface to remove the grooves; and g) secondarily polishing the articular surface until it has a highly polished mirror finish.

11. A method of manufacturing a distal femoral knee prosthesis comprising the steps of:

a) forming a casting that approximates the size and shape of a desired femoral knee prosthesis, the casting including a curved articular surface portion to be finished;

b) grinding the articular surface with a rotary grinding member that cuts multiple elongated grooves in the articular surface of the casting along a predetermined path;

c) moving the casting to present different areas of the articular surface to the grinding surface during the grinding of the articular surface of step "b"; and d) moving the blank and grinding member relative to one another during a cutting of the articular surface;

e) preliminarily polishing the articular surface to remove the grooves; and f) secondarily polishing the articular surface until it has a highly polished mirror finish.

12. The method of claim 11 wherein the rotary grinding member rotates about a first axis and the casting rotates about a second axis, said axes being generally parallel to one another.

13. The method of claim 11 further comprising the step of affixing the casting to a fitment with a central axis, that is rotated about the fitment axis during cutting.

14. The method of claim 11 further comprising the steps of attaching the casting to a fitment and placing an interface material between the fitment and the casting wherein the interface material is softer than the casting at the point of attachment.

15. The method of claim 11 wherein the articular surface includes a pair of condylar surfaces having edge portions and further comprising the step of moving the casting laterally after each elongated groove is cut.

16. The method of claim 11 wherein the step "c", the casting is rotated about a central axis of the casting.

17. The method of claim 14 wherein the interface material is a plastic material.

18. The method of claim 14 wherein the interface material is a polymeric material.

* * * * *

REEXAMINATION CERTIFICATE (3463rd)

United States Patent [19]

Stephens

[11] B1 5,560,096

[45] Certificate Issued  Mar. 10, 1998

[54] METHOD OF MANUFACTURING FEMORAL KNEE IMPLANT

[75] Inventor: Ron Y. Stephens, Memphis, Tenn.

[73] Assignee: Smith & Nephew Richards Inc., Memphis, Tex.

Reexamination Request:
No. 90/004,575, Mar. 6, 1997

Reexamination Certificate for:
Patent No.: 5,560,096
Issued: Oct. 1, 1996
Appl. No.: 376,930
Filed: Jan. 23, 1995

[51] Int. Cl.$^6$ ................................ B23P 13/04
[52] U.S. Cl. ............ 29/558; 29/527.6; 451/21; 623/20
[58] Field of Search ................ 29/527.2, 527.3, 29/527.4, 558, 160.6, 81.11, 56.5, 33 C, 81.01; 451/21, 158, 57, 49; 623/20, 18

[56] References Cited

U.S. PATENT DOCUMENTS

| | | |
|---|---|---|
| 2,269,197 | 1/1942 | Hamilton . |
| 3,412,643 | 11/1968 | Swanson et al. . |
| 4,031,809 | 6/1977 | Shraiman et al. . |
| 4,051,636 | 10/1977 | Heine . |
| 4,510,719 | 4/1985 | Yoneda et al. . |
| 4,599,827 | 7/1986 | Goodwin ............ 451/57 |
| 4,753,044 | 6/1988 | Bula . |
| 4,834,758 | 5/1989 | Lane et al. . |

*Primary Examiner*—L. I. Schmartz

[57] ABSTRACT

A method of manufacturing a distal femoral knee prosthesis includes the initial step of forming a rough prosthesis workpiece member that has the approximate size and shape of a final polished distal femoral prosthesis. The rough prosthesis workpiece member can be a casting, forging or a rough machined part. The prosthesis member is then attached to a fixator and movably supported adjacent a rotary grinder. Relative motion between the rotary grinder and the prosthesis is controlled with a computer. An articular surface of the prosthesis is shaped by engaging the prosthesis with the rotary grinder. The workpiece is primarily polished to remove "scallops" that form on the outer surface during a shaping with the rotary grinder. The prosthesis workpiece member is then secondarily polished until the articular surface provides a highly polished mirror finish.

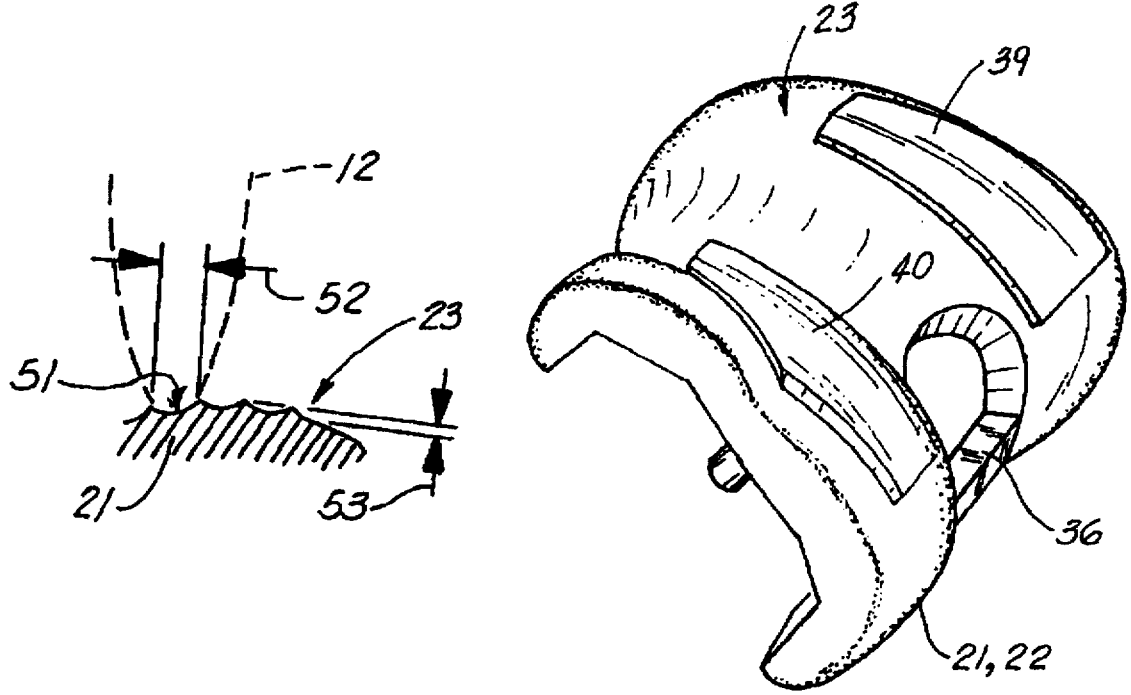

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–18 is confirmed.

\* \* \* \* \*